United States Patent [19]
Nowak et al.

[11] Patent Number: 5,337,231
[45] Date of Patent: Aug. 9, 1994

[54] VIEW TO VIEW IMAGE CORRECTION FOR OBJECT MOTION WITH TRUNCATED DATA

[75] Inventors: Michael P. Nowak; David J. Nowak, both of Greendale, Wis.

[73] Assignee: General Electric Company, Milwaukee, Wis.

[21] Appl. No.: 860,928

[22] Filed: Mar. 31, 1992

[51] Int. Cl.⁵ .................. G06F 15/42; G06K 9/48
[52] U.S. Cl. ................. 364/413.24; 364/413.13; 382/6; 382/44; 378/20
[58] Field of Search .............. 364/413.13, 413.14, 364/413.16, 413.18, 413.22, 413.23, 413.24; 382/6, 44, 45, 42, 54; 378/4, 11, 20, 21; 358/213.11, 213.15, 213.17, 213.29

[56] References Cited

U.S. PATENT DOCUMENTS

| | | | |
|---|---|---|---|
| 4,382,267 | 5/1983 | Angle | 358/213 |
| 4,685,146 | 8/1987 | Fenster et al. | 382/54 |
| 4,858,128 | 8/1989 | Nowak | 364/413.13 |
| 4,870,692 | 9/1989 | Zuiderveld et al. | 382/6 |
| 4,891,767 | 1/1990 | Rzasa et al. | 364/513 |
| 5,048,103 | 9/1991 | Leclerc et al. | 382/44 |
| 5,099,505 | 3/1992 | Seppi et al. | 378/65 |
| 5,128,864 | 7/1992 | Waggener et al. | 364/413.21 |
| 5,170,441 | 12/1992 | Mimura et al. | 382/45 |

Primary Examiner—Roy N. Envall, Jr.
Assistant Examiner—Joseph Thomas
Attorney, Agent, or Firm—Quarles & Brady

[57] ABSTRACT

An apparatus for correcting patient motion between views in a medical imaging device employing multiple views in the generation of an image, and where some view data is truncated as a result of the finite area of the detector array, establishes a last row in the matrix of data for each view prior to and independent of the truncation for the purposes of evaluating motion. The data prior to this last row is compared with the data from the previous view with repeated relative shifts between the data to determine a lowest difference sum. Several difference sums may be employed to determine a shifting amount including a fractional part of a row.

6 Claims, 4 Drawing Sheets

VIEW TO VIEW IMAGE CORRECTION FOR OBJECT MOTION WITH TRUNCATED DATA

BACKGROUND OF THE INVENTION

The present invention relates to medical imaging devices such as nuclear or gamma cameras, as used in nuclear medicine, such imaging devices utilizing separate views taken at different positions to compute a tomographically reconstructed cross-sectional slice image. Specifically, the present invention concerns an apparatus for reducing the effect of motion, between successive views, on the tomographic slice image. The present invention may be also employed in imaging systems other than those used in nuclear medicine, for example, in x-ray computed tomography. For clarity, the following disclosure is directed towards an emission tomographic system.

In one type of emission tomographic imaging system, the single photon emission computed tomography system (SPECT), a low level gamma ray emitter is injected into the body of the patient. The gamma ray emitter is of a type which is absorbed preferentially by an organ whose image is to be produced.

Gamma rays from the gamma ray emitter absorbed by the patient are received by a large area, planar, gamma ray detector. The gamma ray detector incorporates a collimator to receive such radiation predominantly along a direction nominal to its plane. The intensity of the radiation over the plane of the detector is as an array of rows and columns of elements called pixels. Typically, the number of rows will be equal to the number of columns and there are commonly 64 or 128 pixels in each row and column.

A simple projection image may be formed from the array of pixels by assigning each pixel with an image brightness value corresponding to the intensity of the received radiation. Often, however, a tomographic image, or image of a slice through the patient, is preferred.

In tomographic imaging, multiple arrays of pixels are collected as the plane of the gamma ray detector is angled in equal increments in an orbit about an orbit axis through the patient. The two dimensional array of pixels obtained at each angle in the orbit is commonly termed a view. These multiple views are reconstructed according to tomographic reconstruction techniques to produce a set of slice images of adjacent planes perpendicular to the orbit axis. In turn, the reconstructed slice images together can be used to construct a variety of views along various planes within the volume imaged by the gamma ray detector.

Accurate tomographic reconstruction requires that the multiple views be combined so that corresponding pixels between views measure the intensity of radiation from the same volume elements or "voxels" of the patient's body, and that such corresponding pixels differ only in the angle at which the radiation is recorded. Generally, if the body being imaged changes position between successive views, e.g. by sliding along the orbit axis, the reconstructed images may be blurred or contain image artifacts or distortions.

Nevertheless, keeping the patient from moving during the collection of multiple views is not simple. In order to minimize the radiation dosage to which the patient is exposed, the injected gamma ray emitters are of relatively low radioactivity. As a consequence, each view can require up to 40 seconds to obtain. If a total of 64 views on a 360° arc are desired, then the entire imaging process can require more than 40 minutes to complete.

Further, even a small amount of motion can effect the correspondence between pixels of successive views: a single pixel may be as small as ½ centimeter square. Thus, deleterious patient motion and resultant image degradation are common.

The existence of motion between views can usually be detected by examining projection images of the views in rapid succession ("cine mode"). In this case, the movement appears as a sudden jump in an apparently rotating projection image of the patient. Although such an approach may determine whether the collected data is usable, it does not provide a way to eliminate the motion if significant motion exists. Some correction may be performed by visually shifting the images to improve their alignment, but this approach is time consuming and unreliable.

Alternatively, an automated method of detecting and correcting for motion between views is described in U.S. Pat. No. 4,858,128 "View-to-View Image Correction for Object Motion" to Nowak, assigned to the same assignee as that of the present invention and hereby incorporated by reference. In this method, the two dimensional arrays produced in multiple views are collapsed to single one dimensional arrays. The collapsed arrays are then mathematically cross-correlated and the cross-correlation used to determine the relative motion between the views. The motion may then be compensated for by shifting some views with respect to the other views.

Although this automated method generally performs well, it has been determined by the present inventors that it requires the entire region of activity, from which gamma rays are being emitted, to remain within the field of view of the planar gamma ray detector in all views. This requirement is readily met when imaging compact organs, but is not met with images of larger structures such as the brain. In particular, in imaging the head, there can be significant gamma ray emission from the lower portion of the head and from the neck, such regions often extending out of the bottom of the field of view of the planar detector.

It is now recognized that the spatial truncation of the region of activity forms an abrupt discontinuity which is given undue weight in the cross-correlation process and which tends to disproportionately and erroneously influence the determination of motion between views. Generally, the cross-correlation process is misled by the edge of the planar detector, which doesn't move, to the exclusion of pixel data indicating actual patient movement.

SUMMARY OF THE INVENTION

The present invention provides an automated system of detecting and correcting for patient motion among views acquired in an imaging system. The invention addresses, in particular, the situation where the data of the view is spatially truncated by the finite extent of the planar detector.

Generally, the present invention examines only a portion of the array of pixel data, removed from the area of truncation, and employs a matching techniques more amenable to the high noise environment of nuclear medicine.

Specifically, the present invention includes a scanner assembly for collecting a series of views of a patient, including a first and second view. Data from the views may be summed across rows to produce a single column of brightness data, one end of which is truncated at a row limit typically caused by the spatial limitations of the planar detector. A last row number independent of the row limit is selected prior to the row limit and the two views are compared up to this last row to produce a difference sum indicating the difference in brightness between the rows of the first and second view on a row by row basis up to the last row. The views are then shifted to reduce this difference such.

It is thus one object of the invention to accommodate truncated data while automatically detecting and compensating for patient motion. Defining a last row prior to the row limit where truncation occurs, based on the data of the rows and independent of the row number or row limit, allows the error in detected motion caused by the truncation of data to be avoided.

The data of the second view may be normalized to that of the first view and the comparison may employ a subtraction of the data between the rows of the first and second view on a row by row basis and the difference sure derived from a sum of those row by row subtractions.

It is thus another object of the invention to provide a comparison method less susceptible to noise in the array of pixel data than other motion detection methods. The subtraction convergence, produced by the subtraction, summation, comparison, and shifting of the present invention, utilizes data from large areas of the images which makes it more robust against deviations produced by noise. Normalizing the data simplifies this subtraction convergence.

The determination of the last row may be made by evaluating the slope of the data of the rows. It is thus another object of the invention to provide a relatively simple method of selecting a last row number independent of the row limit or of absolute row number.

The amount of shifting between the first and second view is not limited to an integer number of rows but may be extended to fractional parts of rows by interpolating a fractional shift value based on difference sums for the shifted positions of the second view.

Thus it is another object of the invention to provide correction of patient motion to a resolution finer than that of the planar detector.

These and other objects and advantages of the invention will appear from the following description. In the description, reference is made to the accompanying drawings which form a part hereof, an in which there is shown a preferred embodiment of the invention. Such embodiment does not necessarily represent the full scope of the invention and reference is made therefore, to the claims herein for interpreting the scope of the invention.

DETAILED DESCRIPTION OF THE PREFERRED EMBODIMENT

The Scanning System

Figure 1:
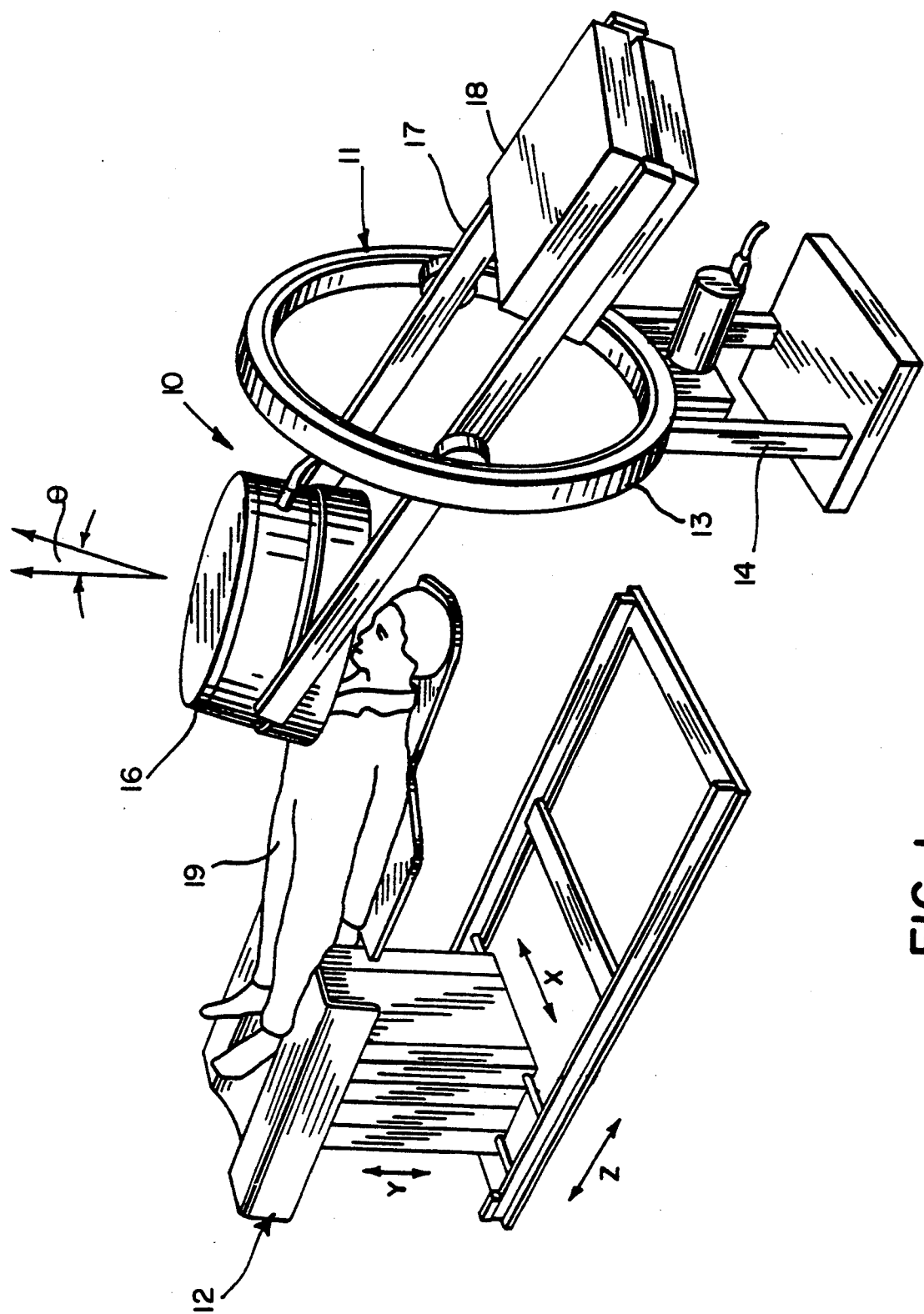
FIG. 1 is a perspective view of a nuclear imaging tomographic scanner which employs the present invention.

Referring to FIG. 1, there is shown, generally at 10, a nuclear imaging tomographic scanning system which includes a tomographic scanner 11, and a patient support table 12. The construction and operation of the scanner 11 is similar to that shown and described in U.S. Pat. No. 4,216,381, issued on Aug. 5, 1980, and assigned to the assignee of the present invention.

Briefly, the scanner 11 comprises an annular gantry 13 supported in a vertical position as shown by a pedestal 14 and having a camera 16 supported from the gantry 13 in cantilevered fashion by an arm assembly 17 and balanced by a counterweight 18 on the other end of the arm assembly 17. The arm assembly 17 is so connected to the gantry 13 as to allow the entire arm assembly 17 to be rotated within the gantry 13 by a motor-drive system (not shown), to thereby rotate the camera 16 in a circular path to a variety of view angles $\theta$, around the patient 19 supported on the table 12. The movement of the camera 16 allows the collection of multiple views which can be used to reconstruct a tomographic image of the patient in the area of concern. The structure and operational movement of the scanner 11 is of a conventional nature.

Figure 2:
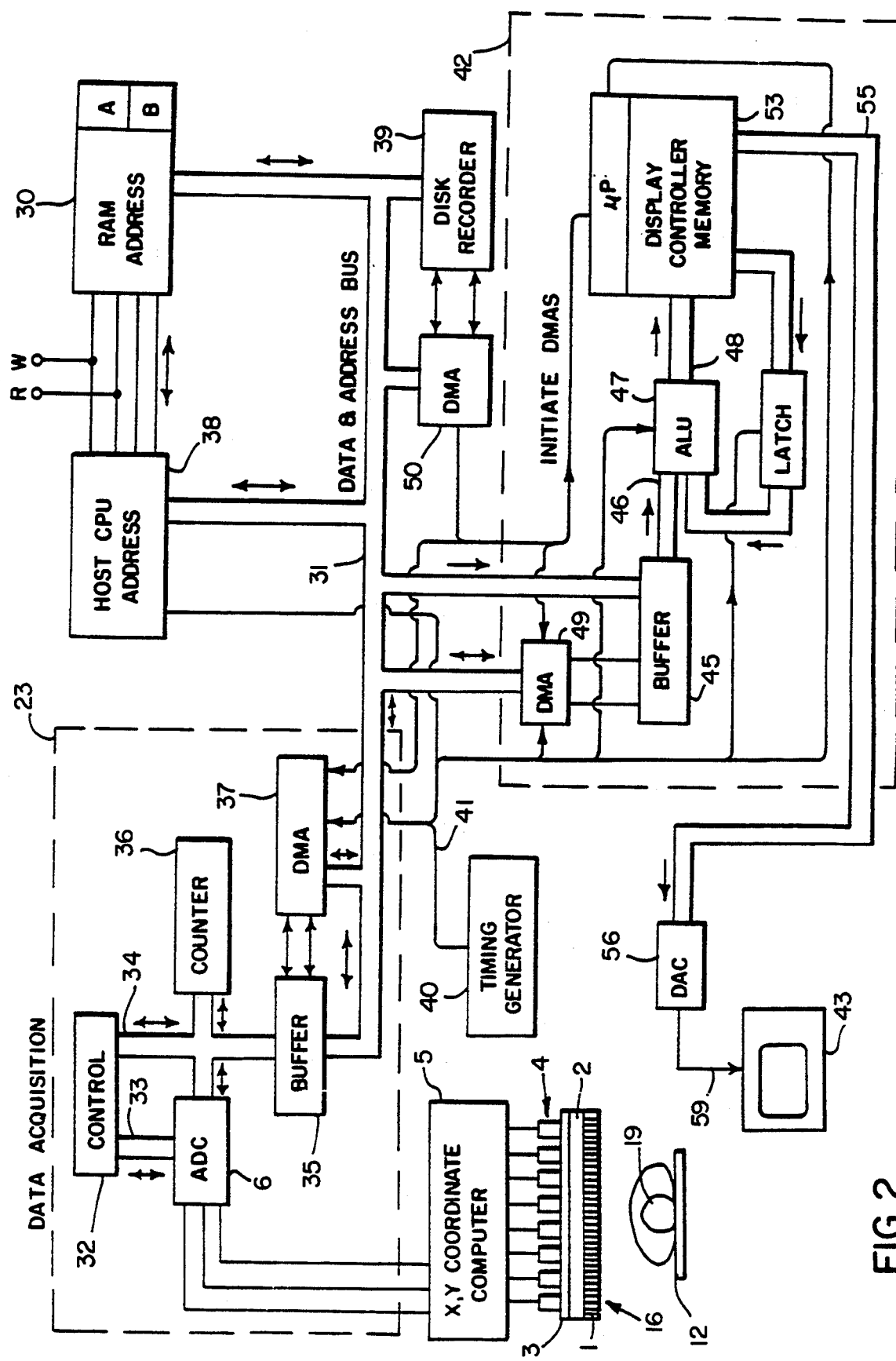
FIG. 2 is an electrical block diagram of the control system for the scanner of FIG. 1.

Referring to FIG. 2, as is well known, the various isotopes used in nuclear medicine are preferentially absorbed by the patient 19 to emit gamma ray photons in a pattern which permits visualizing the configuration of body tissue and blood vessels.

The camera 16 used to detect and identify the coordinates of the gamma ray photon emissions is conventional. The camera comprises a lead plate 1 that has a myriad of fine holes so that the plate acts as a collimator. Interfaced with the collimator is a scintillation crystal 2 which produces scintillations wherever photons are absorbed by it. The scintillations are coupled by means of a glass plate 3 to an array of photomultiplier tubes which are collectively designated by the numeral 4. The photomultiplier tubes are usually packed closely with each other within a circle as is well known.

Data Acquisition Circuitry

Any detected scintillation causes the photomultiplier tubes 4 to produce respective analog signals which are sent to a computer that is symbolized by the block marked 5. The computer 5 uses the signals to compute the x and y coordinates of each scintillation event in terms of analog signal magnitudes. Computing the x and y coordinates in terms of analog signals is well known. One scheme for determnining the x and y coordinates of each scintillation is described in U.S. Pat. No. 4,142,102.

The analog x and y coordinate signals are transmitted from the computer 5 and to analog-to-digital converter (ADC) represented by the block marked 6. A third line running from the computer 5 carries a signal, commonly called a z signal, which is indicative of whether the magnitude of the scintillation pulse was high enough or of the correct isotope to be considered a valid pulse.

ADC 6 is part of a data acquisition module which is within the boundaries of the dashed line 23. The output of ADC 6 to a bus 34 is a series of digital number pairs which correspond to the x and y coordinate, or the addresses, of the scintillations. Each scintillation falls within the boundaries of one of the pixels which define the view. The digital coordinate values are used as addresses to locations in a random access memory (RAM) that is generally designated by the numeral 30 and appear in the upper right portion of FIG. 2.

In the frame mode of operation, every time a pixel location in the memory 30 is addressed, the digital number representing the number of scintillation events at that pixel address is taken out of that location and incremented by one so that at the end of an exposure interval the number in the memory location is representative of the brightness or intensity of the pixel. The buses for transferring data and addresses are represented collectively by a single bus 31 on which the legend "data and address bus" has been applied.

The data acquisition module 23 is involved in the memory location incrementing operation just described. It contains a control that is represented by the block marked 32. It is coupled to ADC 6 with a bidirectional control bus 33 and it also employs the bus 34 which connects to the data and address bus 31 through a buffer 35. There is also an event counter 36 and a direct memory access (DMA) controller 37 in the acquisition module 23. The host central processor or computer for the system is represented by the block marked 38. The host central processor unit 38 will hereinafter be called the CPU for the sake of brevity.

As indicated above, every time a location in RAM 30 is to be incremented by one, the present contents are withdrawn from the affected locations and sent to the control 32 where the digital value is incremented and then returned back to the memory location. The host CPU 38 provides the signals for causing DMA 37 to make the data transfers at the proper time from ADC 6 to RAM 30 and from the RAM 30 to data acquisition control unit 32 for incrementing. Buffer 35 is for the conventional purposes of interchanging data between buses or components in proper timing and for assuring that the data is stabilized before a transfer is made. Counter 36 in data acquisition module 23 is for counting the total number of scintillation events during a particular exposure of study.

As described above, for tomographic acquisitions, a set of two-dimensional images are acquired by the camera 16 over a fixed time interval as it moves in its circular path about the patient to a number of angular positions $\theta$. Each view is a two dimensional array of acquired data which is not only stored in the RAM 30, but also is stored in a disk recorder represented by the block marked 39 and a display controller which is represented by the dashed line block 42. Thus, all of the pixel brightness data for each view is also available from disk recorder 39 at any time.

A sequence of views may be saved without requiring excessive memory capacity in RAM 30, by dividing RAM memory is divided into sectors or blocks which are symbolized by those marked A and B in RAM 30. Thus, pixel data are acquired in a block of memory A for a predetermined time interval determined by CPU 38. After the end of that interval and before the block of memory is overloaded, the pixel data are transferred to disk recorder 39 and to the display controller 42 while at the same time the incoming data from the data acquisition module are switched to the other memory block B so there is no interruption in data acquisition. The acquisition data are repeatedly switched back and forth between blocks A and B in RAM 30 until the host CPU 38 brings about termination of the study. Thus, from the description so far, one may see that the pixel data for a view currently being acquired is in one of the memory blocks A or B and also available, as required from disk recorder 39 and presented for display from the display controller 42. The digital numbers acquired in RAM 30, disk recorder 39, and display controller 42 in the frame mode have a value corresponding to the number of nuclear events which occur at points throughout the volume of interest.

A timing generator symbolized by the block marked 40 is provided for properly timing and synchronizing data and address transfer events in the system. Lines such as the one marked 41 leading out from the timing generator 40 are shown to indicate that the timing function is present.

The display controller 42, has a memory 53 for accepting the pixel or image view data and bringing about display of the data as an image on the CRT which is represented by the block marked 43. When the data for a view has been acquired, it is transferred by way of bus 31 through a buffer 45. The buffer is coupled by way of a bus 46 to an arithmetic logic unit (ALU) which is represented by the block marked 47. The output of ALU 47 is coupled, by means of a bus 48 to an input of display controller memory 53. ALU 47, besides having the capability for adding or subtracting digital pixel data before it enters the display controller, can also let the data from bus 46 flow through without operating on it as it goes to the display controller memory 53. A DMA 49 is also used to control transfer of pixel data from RAM 30 through buffer 45 to ALU 47 at appropriate times. DMA 49 performs the traditional function of notifying the CPU 38 that the data bus 31 is required for making a transfer from RAM 30 to ALU 47 and display memory 53.

Another DMA 50 is associated with disk recorder 39 and its purpose is to transfer data in and out of disk recorder 39 at the proper times. DMA 50 can be used to control transfer of data from RAM memory 30 to the disk recorder 39 as mentioned above and it can also control transfer of data from disk recorder 39 to RAM 30 when one desires to display a sequence of images that are stored on disk.

Assume now that the pixel data for a view is now in the memory 53 of the display controller 42. Typically the display controller memory has a 64×64 or a 128×128 pixel array. The intensity of radiation received at each pixel is represented by the value of a digital number in the respective display controller memory locations. The digital values must be converted to analog video signals for permitting display on CRT 43. Typically, the bit range of the display controller memory locations is 12-bits. The 12-bit digital values are transferred in sequence by way of a bus 55 to a digital-to-analog converter or, DAC 56, where the digital data is converted to analog video signals which are sent by means of a cable 59 to CRT 43 to effectuate display of the image.

At the completion of a scan of the patient, disk recorder 39 stores a data set for a plurality of views. Each view includes sufficient data to reproduce a two-dimensional projection image on the display 43 which represents the intensity of the scintillation events as seen from one of a plurality of the camera viewing planes disposed around the patient. Computed tomography is then employed to reconstruct from this acquired data the slices taken through a volume of interest. The slices are parallel to each other and they are evenly spaced apart along the third dimension (Z axis). As is well known in the art, this data set can be transformed in the CPU 38 to reorient the slices along any axis such that a series of two-dimensional images taken through the patient at any point and at any angle can be reconstructed.

Motion Detection and Correction

During the acquisition of multiple views, the patient 19 may shift on the table 12 predominantly along the Z axis as indicated in FIG. 1. The present invention is a method for detecting and reducing the effects of such shifting between adjacent views as acquired by the scanning system 10.

Figure 3:
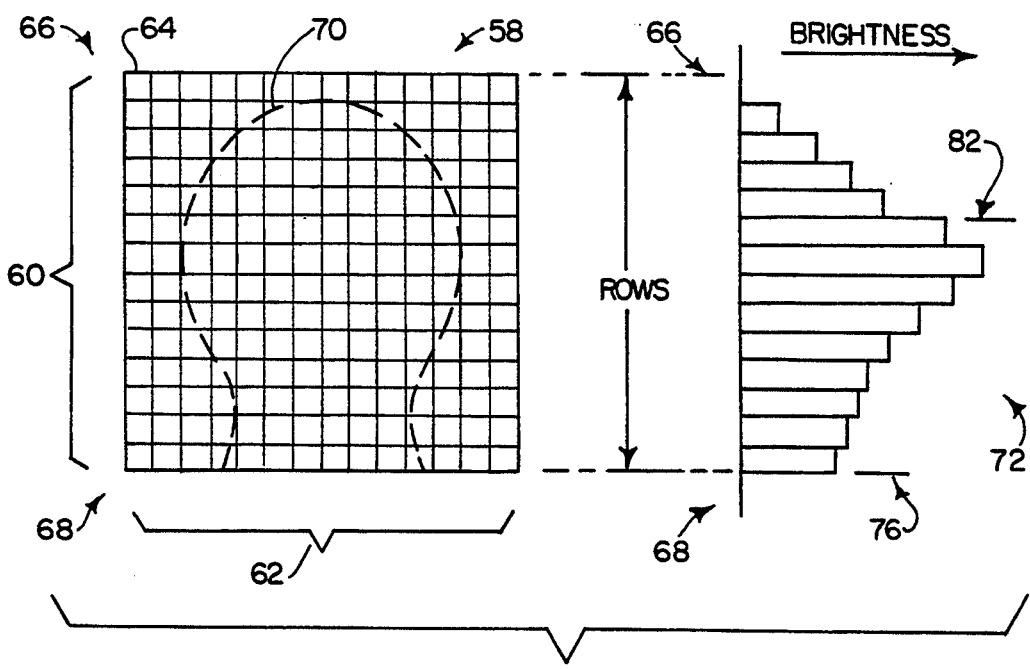
FIG. 3 is a graphic representation of a two dimensional array of pixel data acquired in a single view with the scanner of FIG. 1 and that data as compressed to a line histogram.

Referring now to FIGS. 1, 2 and 3, a single view 58 as held in RAM 30 may be visualized as rows 60 and columns 62 of pixel data 64 holding the brightness information acquired from the camera 16 at a given gantry angle $\theta$ as previously described. The rows will be considered to lie perpendicular to the patient 19's medial, superior to inferior, axis with the columns lying transverse to the rows. The rows may be conveniently identified as superior 66 or inferior 68 as dictated by the orientation of the patient 19 with respect to the camera head 16 to conform with the superior and inferior aspects of the patient, and the columns as left or right accordingly.

For a given view 58, certain centrally located pixels 64 may exhibit an brightness above a background level and thus define a region of activity 70. Generally, the pixels outside of this region of activity 70 will have brightness readings perturbed only by noise.

In the imaging of certain organs within patient 19, the region of activity 70 will be spatially compact and bordered on all sides by pixels 64 having low brightness readings. The data of such a view is considered "non-truncated" because the entire region of activity is within the spatial extent of the view 58. This generally means that the region of activity 70 is smaller than the physical extent of the camera 16 and its array of scintillation crystals 2.

In the imaging of larger regions of activity such as the patient's head, the region of activity 70 may be greater than the spatial extent of the view 58. In particular, the pixels 64 of the view 58 may have significant brightness in the inferior rows 68 corresponding to the region of the patient's neck. Thus, generally for head imaging, the region of activity 70 extends beyond the inferior rows 68 of the view 58 and may be said to be truncated.

As discussed above, this truncation provides an artificially abrupt edge to the data of the view 58 which may fool motion detection methods. This truncated edge suggests that a patient 19 is not moving along the superior to inferior axis, or Z axis because of the edge's apparent stability with respect to the camera 16. The present invention finds primary use in such truncated views 58 where the region of activity 70 is truncated at one edge.

Figure 4:
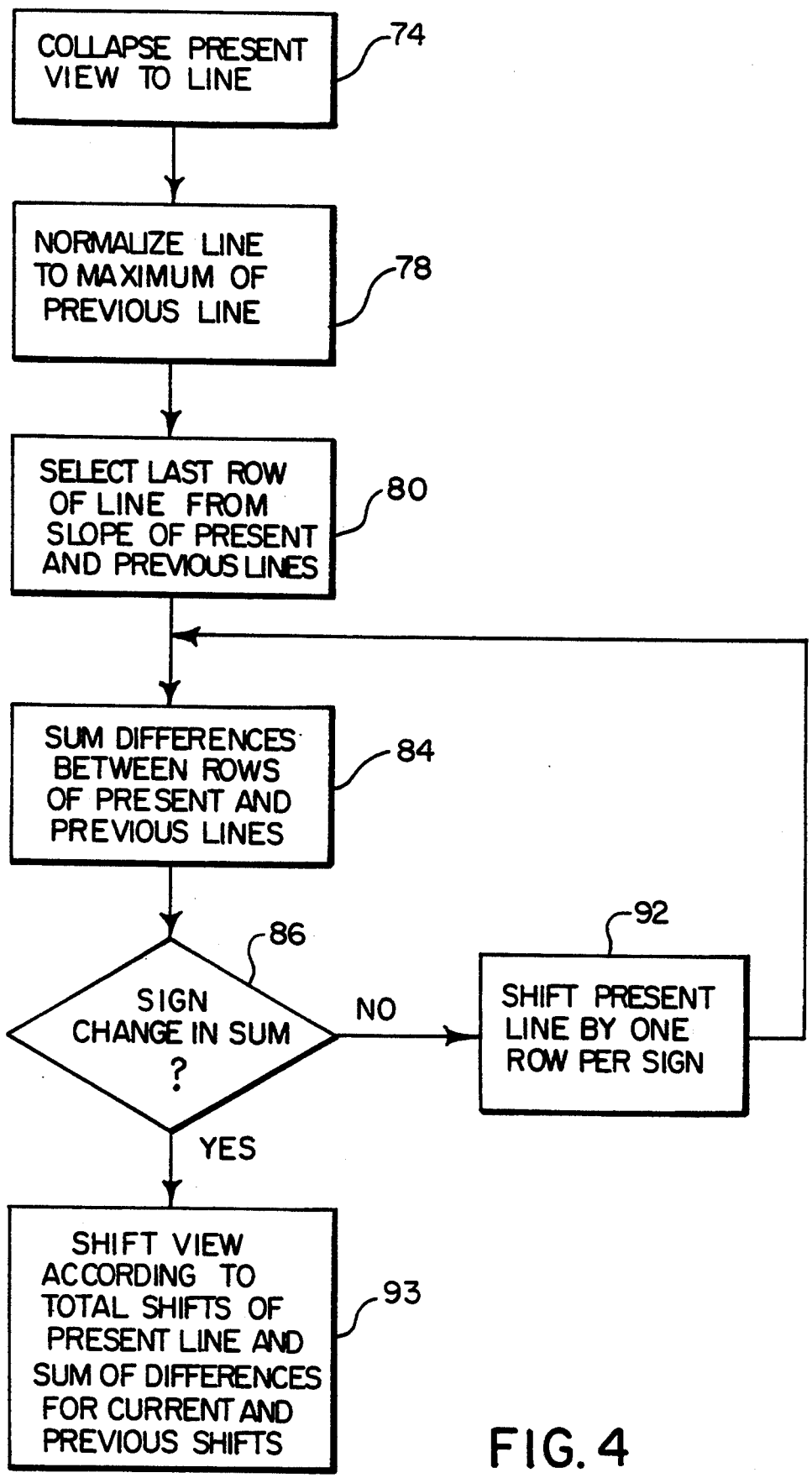
FIG. 4 is a flow chart of the operation of the motion detection and correction apparatus of the present invention.

The invention processes the acquired views 58 in numerical form on CPU 38 to correct those views for motion according to the procedure indicated in FIG. 4. Referring then to FIG. 4 as well as FIGS. 1 and 3, each view 58, as acquired by the scanning system 10, is collapsed to a line histogram 72 as indicated by process block 74. This collapsing process involves summing together the brightness values of the pixels 64 across the columns of the view 58 to provide a one dimensional array having the same number of rows as the view 58 but only a single representative column also having superior and inferior rows 66 and 68. The rows are numbered by convention consecutively from the superior row 66 to the inferior row 68.

This collapsing process not only reduces the amount of pixel data that must be handled in detecting motion but also serves to reduce the effect of noise in each pixel 64 on the total process. It has the additional feature of reducing the effect of any truncation of the data of the region of activity 70 at its left and right edges, any such truncation being reduced in effect by the summation process. The line histogram 72 exhibits a truncation edge 76 having high brightness values at the inferior rows 68.

At process block 78 the line histogram 72 is normalized to the maximum value of a previous line histogram $72_{n-1}$ formed from a previous view $58_{n-1}$ (not shown) if a previous view $58_{n-1}$ exists. If there has been no previous view $58_{n-1}$ (for the first view to be processed, for example), this step 78 is skipped, that is the line histogram 72 is not normalized or effectively normalized to a value of 1.

Assuming there has been a previous view $58_{n-1}$, the brightness value of each row of the line histogram 72 is multiplied by a ratio of the maximum value of the previous line histogram $72_{n-1}$ divided by the maximum value of that line histogram 72. That is:

$$b'_i = b_i \frac{MAX_{n-1}}{MAX_n} \qquad (1)$$

where $b'_i$ and $b_i$ are the brightness values of the ith row of the present histogram 72 before and after normalization and $MAX_n$ and $MAX_{n-1}$ are the maximum values of the present and previous histograms 72 and $72_{n-1}$.

At process block 80, the present histogram 72 is analyzed from the superior row 66 to the inferior row 68 to determine a row of maximum positive slope 82. It is assumed in this analyses that the data of the superior row 66 is not truncated and this assumption is enforced by the proper positioning of patient 19. It is also assumed that the maximum total brightness for the histogram lies between the inferior and superior rows. Thus the row of maximum slope 82 provides a convenient fiducial reference with respect to the patient 19 occurring before the inferior row 68 and the truncation 76. Important, the row of maximum slope is independent of the truncation point 76 and of the absolute row number of the line histogram 72 but dependant primarily on the position of the patient 19.

If there is not previous view $58_{n-1}$, the program proceeds to the next view and returns to process block 74. This follows simply from the fact that the subsequent steps of motion correction between views 58 requires at least two views. All views are corrected so that they are aligned with the first view. The first view is not corrected.

Figure 5A:
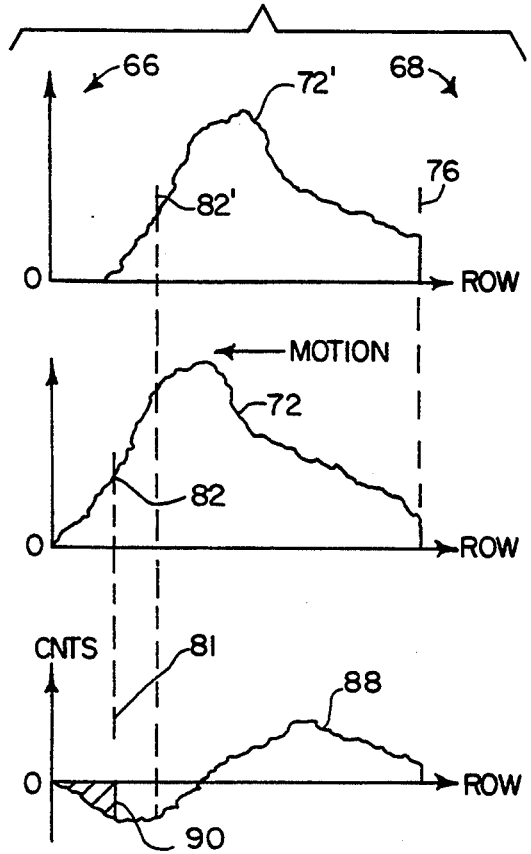
FIGS. 5(a) and (b) are sets of graphs showing line histograms for two views shifted in opposite directions and showing the difference sums produced by this relative motion.
Figure 5B:
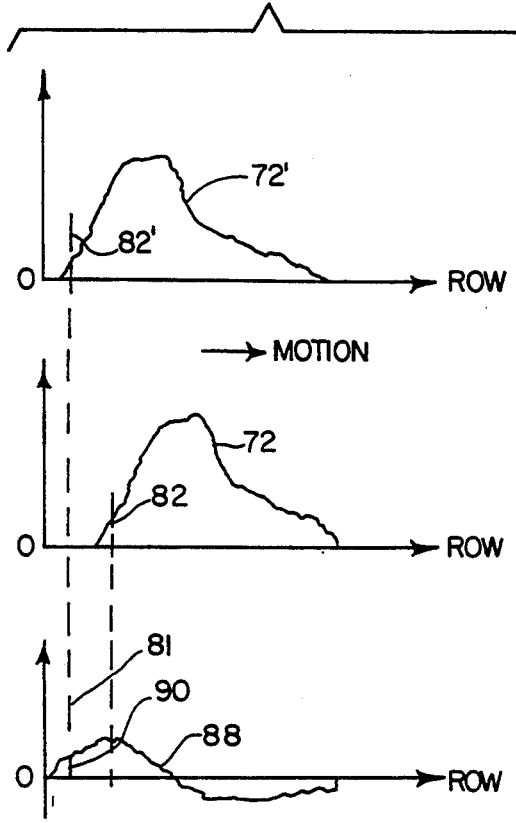

Referring to FIGS. 5(a) and 5(b), if there is a previous view $58_{n-1}$ the row of maximum slope 82 for the present histogram 72 is compared to the row of maximum slope $82_{n-1}$ computed from the previous histogram $72_{n-1}$, at process block 80. A last row number 81 is then established corresponding to the row of maximum slope 82 or $82_{n-1}$ whichever has the smaller row number.

The brightness values for each row of the line histogram 72 are subtracted from the brightness values of corresponding rows of the line histogram $72_{n-1}$ to create a difference histogram 88. That is:

$$d_i = b_{(i+a)(n-1)} - b'_{(i+c)(n)} \qquad (2)$$

where $d_i$ is the value of the ith row of the difference histogram 88 and $b'_{i(n)}$, and $b_{i(n-1)}$ are the normalized brightness values of the present and the unnormalized values of the previous histograms 72 and $72_{n-1}$ and a and c are shifting constants to be explained below. A difference sum is then computed being the sum of the values $d_i$ over each row i of the difference histogram or:

$$\text{difference sum} = \sum_{i}^{\text{last row}} d_i \qquad (3)$$

The computation of the difference sum is shown in FIG. 4 as process block 84.

For the first such comparison, the difference histogram is computed by subtracting those rows having the same row number i in the line histograms 72 and $72_{n-1}$. That is, the shift constants a and c in equation (2) are zero. Thus, the brightness value of row i=0 of line histogram 72 is subtracted from the brightness value of row i=0 of line histogram $72_{n-1}$.

As shown in FIG. 5(a), patient motion in the superior direction has occurred between the acquisition of the previous view $58_{n-1}$ and a later views 58 associated with line histograms $72_{n-1}$ and 72 The difference histogram is computed from the superior row at i=0 and the area under the curve generated by the difference histogram values is summed from 0 to last row 81 to produce a difference sum 90. In this case, where the present histogram 72 exhibits superior motion with respect to the previous histogram $72_{n-1}$, the difference sum 90 will be negative.

In comparison, in FIG. 5(b), the present histogram 72 has exhibits relative inferior motion with respect to the previous histogram $72_{n-1}$ and the difference sum 90 is positive.

It will be noted that in both FIG. 5(a) and 5(b) the histograms 72 and $72_{n-1}$ are not identical because they represent views taken at different angles $\theta$.

Referring now to FIG. 4, at decision block 86, the sign of the difference sum 90 is evaluated and it is compared to the sign of a previous difference sum calculated, if any. The first time decision block 86 is reached, there will be no previous sign against which to compare the sign of the present difference sum and therefore the process jumps directly to process block 92 as described below. For subsequent loops through decision block 86, if the sign of the present difference sum is different from the sign of the difference sum previously evaluated at process block 84, then the process advances to process block 93, otherwise the process advances to process block 92.

If, at process block 92, the sign of the difference sum is positive, indicating an inferior motion in the present line histogram 72, then prior to computing the difference value at equation (2) and (3) in block 84, the brightness data of each row of either line histogram 72 or line histogram $72_{n-1}$ is effectively moved one row in the superior direction by incrementing either constants a or c in equation (2). If the sign of the difference sum 90 is negative, a is incremented and the histogram $72_{n-1}$ is moved one row in the superior direction. If the sign of the difference sum 90 is positive, c is incremented and the histogram 72 is moved one row in the superior direction.

As the histograms are shifted in the superior direction, the brightness data will move beyond the actual rows defining the views 58, for example, the brightness data in the superior most row 64 will move outside the view in a superior direction. For practical purposes, this data is simply ignored and will not be used in the calculation of the difference sum which concerns only the data from 0, up to the last row 81 in that histogram which is not being shifted as previously described. The last row 81 remains fixed with respect to the absolute row number in the unshifted histogram.

After the shifting represented by process block 92 in FIG. 4, the difference histogram 88 is again calculated between the histograms 72 and $72_{n-1}$ with the new value of a or c per equation (2) as indicated in process block 84. At decision block 86, the sign is again evaluated with respect to the sign of the previous difference sum 90 at process block 86.

This loop formed from process blocks 84, 86 and 92 continues for as long as the present difference sum 90 has the same sign as the previous difference sum 90 indicating that the shifted histogram 72 or $72_{n-1}$ should continue to be shifted in the same direction. At some point the different value 90 will change in sign indicating that the histogram has been shifted one row too far and has passed the point of maximum alignment with the other histogram as indicated by the present method. At this time the present difference sum 90 and the previous difference sum 90, immediately prior to the last performance of process block 84, are saved as $sum_1$ and $sum_2$, respectively and decision block 86 directs the process to process block 93.

The values of $sum_1$ and $sum_2$, together with the direction and total number of shifts performed at process block 92 indicated by shift constant a or c, are used to establish a correction factor to be applied to the present view 58. Simply, the present view 58 is shifted up or down to align it to the previous view. It is shifted by one less than the number of shifts c, if up, a, if down, performed on its histogram 72. That one less shift is performed reflects the fact that the histogram was in fact shifted too far in order to trigger the detection of a change in sign.

In a further embodiment, a fractional shift of the view 58 may be performed by computing a ratio of $sum_2$ divided by $sum_2$ minus $sum_1$. Thus, the total shift S is

TABLE I

| If down | If up |
|---|---|
| $S = (a - 1) + \dfrac{sum_2}{sum_2 - sum_1}$ | $S = (c - 1) + \dfrac{sum_2}{sum_2 - sum_1}$ |

This fractional shift is effected simply by shifting the pixel data of view 58 by $a-1$ or $c-1$ and then interpolating between the pixel data of adjacent rows to an interpolation point indicated by the fraction $$\frac{\text{sum}_2}{\text{sum}_2 - \text{sum}_1}.$$

That is, after the shift a−1, or c−1 new brightness data is generated for each row i of the view 58 according to the following formula $$b(i,j) = \frac{\text{sum}_2}{\text{sum}_2 - \text{sum}_1} b(i \pm 1, j) + \left(1 - \frac{\text{sum}_2}{\text{sum}_2 - \text{sum}_1}\right) b(i,j) \quad (5)$$

where i and J are row and column values respectively in view 58 and the sign of i±1 is determined from the direction of the fractional shift.

It will be apparent to those of ordinary skill in the art from the above description that many variations are possible from the preferred embodiment. For example, the present system may be employed after preprocessing of the view data 58 according to methods well known in the art. Also, the number of rows and columns of the view data may be changed according to the resolution of the camera. In order to apprise the public of the various embodiments that may fall within the scope of the invention, the following claims are made.

I claim:

1. An apparatus for correcting patient motion occurring along an axis between views, in an imaging apparatus employing multiple views in constructing an image, the apparatus comprising:
   a detector for collecting a first and second view of an object, the first and second views including brightness data having values in order rows along the axis, the brightness data truncated by the detector for rows beyond a row limit;
   a means for establishing a last row number common to the first and second views, before the row limit and independent of the row limit;
   a comparator for comparing the brightness of the data of each row of the first view with the brightness of the data of each corresponding row of the second view only for rows before the row limit to produce a difference sum indicating the similarity of values of said brightness data between the first and second views;
   a shifter for shifting the brightness data in the corresponding row of the second view by a number of rows so that the difference sum indicates the greatest similarity in the correspondingly ordered values of said brightness data between the first and second rows; and
   a view corrector repositioning the second view by the number of rows to correct patient motion in the second view.

2. The apparatus of claim 1 including means for normalizing the brightness data of the second view to the brightness data of the first view.

3. The apparatus of claim 2 wherein the comparator subtracts the brightness data of each row of the first view from the brightness of the data of each corresponding row of the second view, for rows before the row limit, to produce a component difference for each row having a magnitude and sign and then sums the component differences observing both magnitudes and signs to produce the difference sum indicating the similarity of such brightness data.

4. The apparatus of claim 1 wherein
   the first and second views also include brightness data in columns perpendicular to the rows; and
   including an adder for summing the column data together for each row to produce the brightness data for the first and second rows.

5. The apparatus of claim 4 wherein the means for establishing the last row number selects the first row between the first and second views having the greatest change in brightness from a preceding row of that view with respect to each pair of rows of that view.

6. The apparatus of claim 1 including additionally:
   a means for generating a fractional shift number based on an evaluation of the difference sums associated with the shifted second view; and
   an interpolator for interpolating from the brightness data in the corresponding rows of the second view, new brightness data at a point equal to the fractional shift between the corresponding rows of the second view.

* * * * *